US008476024B2

(12) United States Patent
Mahrhold et al.

(10) Patent No.: US 8,476,024 B2
(45) Date of Patent: Jul. 2, 2013

(54) BOTULINUM NEUROTOXIN A PROTEIN RECEPTOR AND USES THEREOF

(75) Inventors: Stefan Mahrhold, Hannover (DE); Johannes Wilhelm Bigalke, Hannover (DE); Andreas Rummel, Hannover (DE); Thomas Binz, Hannover (DE)

(73) Assignee: Toxogen GmbH, Hannover (DE)

( * ) Notice: Subject to any disclaimer, the term of this patent is extended or adjusted under 35 U.S.C. 154(b) by 249 days.

(21) Appl. No.: 12/084,074

(22) PCT Filed: Oct. 30, 2006

(86) PCT No.: PCT/EP2006/010420
§ 371 (c)(1),
(2), (4) Date: Aug. 22, 2008

(87) PCT Pub. No.: WO2007/048638
PCT Pub. Date: May 3, 2007

(65) Prior Publication Data
US 2009/0252722 A1    Oct. 8, 2009

(30) Foreign Application Priority Data

Oct. 28, 2005  (DE) .......................... 10 2005 051 789

(51) Int. Cl.
G01N 33/53    (2006.01)
G01N 33/567   (2006.01)
A61K 38/00    (2006.01)
A61K 39/00    (2006.01)

(52) U.S. Cl.
USPC ............ 435/7.1; 435/7.2; 435/7.21; 530/300; 530/324; 530/350; 424/184.1; 424/185.1

(58) Field of Classification Search
None
See application file for complete search history.

(56) References Cited

FOREIGN PATENT DOCUMENTS

| WO | WO 2004/051222 | * | 6/2004 |
|----|----------------|---|--------|
| WO | WO 2005/016233 | A2 | 2/2005 |
| WO | WO 2007/050390 |   | 5/2007 |

OTHER PUBLICATIONS

Jarvik et al. Annu. Rev. Genet,. 1998. 32:601-618.*
Notification of Transmittal of the International Search Report or the Declaration (with English Translation) of PCT/EP2006/010420, mailed Apr. 10, 2007.
English Translation of the Written Opinion of PCT/EP2006/010420, mailed Jun. 11, 2008.
English Translation of Notification of Transmittal of International Preliminary Examination Report of PCT/EP2006/010420, mailed Jun. 19, 2008.
Altschul, Stephen F., et al., "Basic Local Alignment Search Tool", *J. Mol. Biol.*, 215:403-410, 1990.
Curtis, R.A.J., EBI Accession No. GSP: ABP98503, "New Isolated 46584 nucleic acid molecule and polypeptide, useful for the diagnosis and treatment of 46584-related pathologies, such as cancer, cardiovascular, autoimmune, neurological, metabolic and inflammatory disorders", for rat synaptic vesicle protein 2c [*Rattus norvegicus*]XP002 423500 [online], May 20, 2003 [retrieved on Apr. 16, 2008]. Retrieved from the Internet:<http://stnweb.cas.org/cgi-bin/sdcgi?SID=760181-1532422783-200&APP=stnweb&>.
Devereux, John, et al., "A Comprehensive Set of Sequence Analysis Programs for the VAX", *Nucleic Acids Research*, 12(1):387-395, 1984.
Dong, Min, et al., "SV2 is the Protein Receptor for Botulinum Neurotoxin A", *Science*, 312:592-596, 2006.
GenPept Accession No. NP_055794 for synaptic vesicle glycoprotein 2c [*Homo sapiens*] [online], Feb. 10, 2008 [retrieved on Apr. 15, 2008]. Retrieved from the Internet:< http://www.ncbi.nlm.nih.gov/entrez/viewer.fcgi?db=protein&id=73695465>.
GenPept Accession No. NP_113781 for synaptic vesicle glycoprotein 2c [*Rattus norvegicus*] [online], Feb. 10, 2008 [retrieved on Apr. 15, 2008]. Retrieved from the Internet:< http://www.ncbi.nlm.nih.gov/entrez/viewer.fcgi?db=protein&id=13928804>.
GenPept Accession No. XP_127490 for Predicted: synaptic vesicle protein 2C isoform 1 [*Mus musculus*] [online], Jan. 11, 2006 [retrieved on Apr. 15, 2008]. Retrieved from the Internet:< http://www.ncbi.nlm.nih.gov/entrez/viewer.fcgi?db=protein&id=82952023>.
Gimenez, Juan A. and Dasgupta, B.R., "Botulinum Type A Neurotoxin Digested with Pepsin Yields 132, 97, 72, 45, 42 and 18 kD Fragments", *J. Protein Chem.*, 12(3): 351-363, 1993.
Habermann, E., et al., "Tetanus Toxin Blocks the Neuromuscular Transmission in vitro Like Botulinum A Toxin", Naunyn-Schmiedeberg's Archives of Pharmacology, 311:33-40, 1980.
Henikoff, Steven, et al., "Amino Acid Substitution Matrices From Protein Blocks", *Proc. Natl. Acad. Sci. USA*, 89:10915-10919, 1992.
Herreros, Judit, et al., "C-Terminal Half of Tetanus Toxin Fragment C is Sufficient for Neuronal Binding and Interaction With a Putative Protein Receptor", *Biochem. J.*, 347:199-204, 2000.
Janz, R., et al., "SV2C is a Synaptic Vesicle Protein With an Unusually Restricted Localization: Anatomy of a Synaptic Vesicle Protein Family", *Neuroscience*, 94(4):1279-1290, 1999.
Lacy, D. Borden, et al., "Crystal Structure of Botulinum Neurotoxin Type A and Implications for Toxicity", *Nature Structural Biology*, 5(10):898-902, 1998.
Mahrhold, Stefan, et al., "The Synaptic Vesicle Protein 2C Mediates the Uptake of Botulinum Neurotoxin A Into Phrenic Nerves", *FEBS Letters*, 580:2011-2014, 2006.
Needleman, Saul B., et al., "A General Method Applicable to the Search for Similarities in the Amino Acid Sequence of Two Proteins", *J. Molecular Biology*, 48:443-453, 1970.
Rummel, Andreas, et al., "Synaptotagmins I and II Act as Nerve Cell Receptors for Botulinum Neurotoxin G*", *J. of Biol. Chem.*, 279(29):30865-30870, 2004.

(Continued)

Primary Examiner — Oluwatosin Ogunbiyi
(74) *Attorney, Agent, or Firm* — Carol L. Francis; Bozicevic, Field & Francis LLP

(57) ABSTRACT

The invention relates to an isolated polypeptide of the luminal domain of synaptic vesicle glycoprotein 2C of *Homo sapiens* wherein at least 70 percent of the amino acid sequence is identical to the amino acid sequence of the SV2C of *Homo sapiens*. The polypeptide binds the $H_C$ fragment of botulinum neurotoxin A provided that the polypeptide is not the synaptic vesicle glycoprotein 2C of *Homo sapiens*.

24 Claims, 2 Drawing Sheets

OTHER PUBLICATIONS

Figure 1:
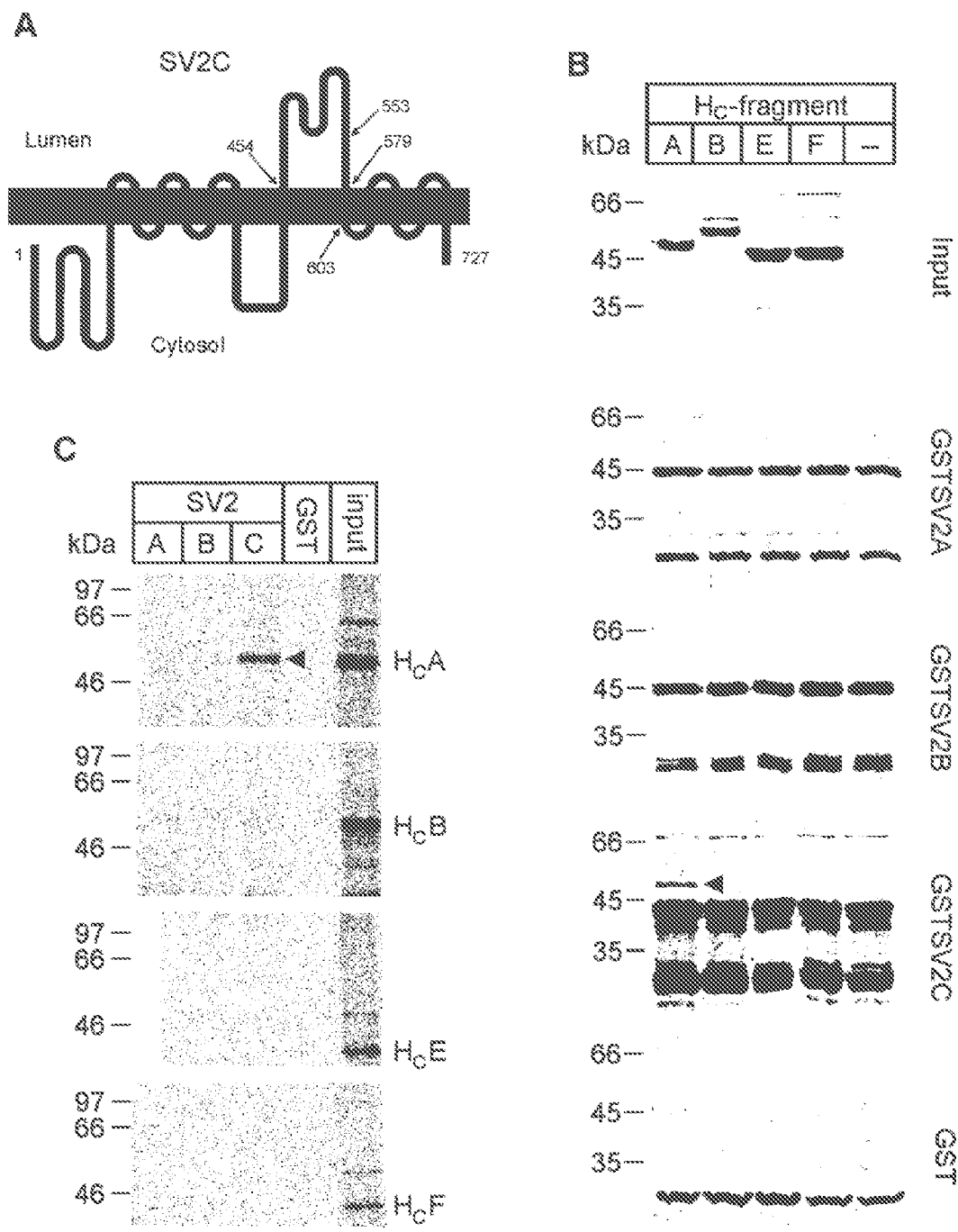

Rummel, Andreas, et al., "The $H_{cc}$-Domain of Botulinum Neurotoxins A and B Exhibits A Singular Ganglioside Binding Site Displaying Serotype Specific Carbohydrate Interaction", *Molecular Microbiology,* 51(3):631-643, 2004.

Shone, Clifford C., et al., "Inactivation of *Clostridium botulinum* Type A Neurotoxin by Trypsin and Purification of Two Tryptic Fragments", *Eur. J. Biochem,* 151:75-82, 1985.

Lynch et al., 2003, "The synaptic vesicle protein SV2A is the binding site for the antiepileptic drug levetiracetam", PNAS, 101(26), 9861-9866.

Nowakowski et al. (2002) "Potent Neutralization of Botulinum Neurotoxin by Recombinant Oligoclonal Antibody" Proc Natl Acad Sci 99(17):11346-11350.

* cited by examiner

BOTULINUM NEUROTOXIN A PROTEIN RECEPTOR AND USES THEREOF

RELATED APPLICATIONS

This application is the U.S. National Stage of International Application No. PCT/EP2006/010420, filed Oct. 30, 2006, published in German, and claims priority under 35 U.S.C. §119 or 365 to German Application No. 10 2005 051 789.7, filed Oct. 28, 2005.

The present invention relates to a polypeptide binding the botulinum neurotoxin A (BoNT/A) formed by *clostridium botulinum*. This polypeptide is a polypeptide consisting of an amino acid sequence, at least 70 percent of which is identical to the amino acid sequence of the synaptic vesicle glycoprotein of *homo sapiens*, so that the polypeptide binds the $H_C$-fragment of botulinum neurotoxin A provided that the polypeptide is not the synaptic vesicle glycoprotein 2C of *homo sapiens*. The present invention further relates to the peptide sections of the SV2C protein interacting with BoNT/A. In particular, the invention relates to the use of the polypeptide and the peptide sections thereof as an antagonist for reducing the neurotoxicity of BoNT/A, as an expedient for identifying substances which reduce binding of BoNT/A to nerve cells and for detecting BoNT/A in different matrices.

Nerve cells release transmitter substances by exocytosis. The fusion of the membranes of intracellular vesicles with the plasma membrane is referred to as exocytosis. In the course of this process the vesicular content is simultaneously released into the synaptic gap. The fusion of the two membranes is regulated by calcium, reacting with the protein synaptotagmin. Jointly with other co-factors synaptotagmin controls the status of three so-called fusion proteins, SNAP-25, synaptobrevin 2 and syntaxin 1A. While syntaxin 1A and synaptobrevin 2 are integrated into the plasma and/or vesicle membrane, SNAP-25 binds only lightly to the plasma membrane. To the extent that the intracellular calcium concentration increases, the three proteins bind to one another, both membranes approaching one another and subsequently fusing together. In the case of cholinergic neurons acetyl choline is released; causing muscle contractions, perspiration and other cholinergically provoked reactions.

The above mentioned fusion proteins are the target molecules (substrates) of the light chain (LC) of the clostridial neurotoxins, formed by the bacteria *C. botulinum, C. butyricum, C. baratii* and *C. tetani*.

The anaerobic, gram-positive bacterium *C. botulinum* produces seven different serotypes of the clostridial neurotoxins. The latter are referred to as the botulinum neurotoxins (BoNT/A to BoNT/G). Among these, in particular BoNT/A and BoNT/B cause a neuroparalytic disorder in humans and animals, referred to as botulism. The spores of *C. botulinum* can be found in the soil, but may also develop in inexpertly sterilised and sealed home-made food preserves, to which many cases of botulism are attributed.

BoNT/A is the most active of all known biological substances. As little as 5-6 pg of purified BoNT/A represent an MLD (Minimal Lethal Dose). One unit (Engl.: Unit, U) of BoNT/A is defined as the MLD, killing half of the female Swiss Webster mice, each weighing 18-20 g, after intraperitoneal injection. Seven immunologically different BoNTs were characterised. They are denoted as BoNT/A, B, C1, D, E, F and G and may be distinguished by neutralisation with serotype-specific antibodies. The different serotypes of BoNTs differ in affected animal species with regard to severity and duration of the paralysis caused. Thus, with regard to paralysis, BoNT/A is 500 times more potent in rats for example, than BoNT/B. In addition, BoNT/B has proved to be non-toxic in primates at a dosage of 480 U/kg of body weight. The same quantity of BoNT/A corresponds to 12 times the lethal dose of this substance in primates. On the other hand, the duration of paralysis after BoNT/A injection in mice is ten times longer than after injection of BoNT/E.

BoNTs are used for treating neuromuscular disorders, characterised by hyperactivity in skeleton muscles, caused by pathologically overactive peripheral nerves. BoNT/A has been approved by the U.S. Food and Drug Administration for treating blepharospasm, strabism, hyperhidrosis, wrinkles and hemi-facial spasms. Compared to BoNT/A the remaining BoNT serotypes are evidently less efficacious and manifest a shorter duration of efficacy. Clinical effects of BoNT/A administered peripheral-intramuscularly are usually noticeable within a week. The duration of symptom suppression by one single intramuscular injection of BoNT/A is normally about three to six months.

The clostridial neurotoxins specifically hydrolyse different proteins of the fusion apparatus. BoNT/A, C1 and E break up SNAP-25, while BoNT/B, D, F, G as well as tetanus neurotoxin (TeNT) attack the vesicle-associated membrane protein (VAMP) 2—also referred to as synaptobrevin 2—. BoNT/C1 furthermore breaks up syntaxin 1A.

The *Clostridium* bacteria release the neurotoxins as single-chain polypeptides each having 1251 to 1315 amino acids. Thereafter endogenous proteases split each of these proteins at a defined location into 2 chains each ('nicking'), the two chains however remaining interlinked by a disulphide-bridge. These dual-chain proteins are referred to as holotoxins (see Shone et al. (1985), Eur. J. Biochem. 151, 75-82). The two chains have different functions. While the smaller fragment, the light chain (light chain=LC), represents a $Zn^{2+}$-dependent endoprotease, the larger unit (heavy chain=HC) represents the transporting means of the light chain. By treating the HC with endopeptidases two 50 kDa fragments were brought about (see Gimenez et al. (1993), J. Protein Chem. 12, 351-363). The amino-terminal half ($H_N$-fragment) integrates into membranes at a low pH-value and translocates the LC into the cytosol of the nerve cell. The carboxyl-terminal half ($H_C$-fragment) binds to complex polysialogangliosides, occurring exclusively in nerve cell membranes and to protein receptors identified only partially to date. The latter explains the high neuroselectivity of the clostridial neurotoxins. Crystalline structures confirm that BoNT/A disposes of three domains, which may be harmonised by the three steps of the action mechanism (see Lacy et al. (1998), Nat. Struct. Biol. 5, 898-902). Moreover, these data give rise to the conclusion that within the $H_C$-fragment two autonomous subunits (sub-domains) exist of 25 kDa each. The first proof for the existence of the two functional sub-domains was brought about by the amino-terminal ($H_{CN}$) and the carboxyl-terminal half ($H_{CC}$) of the $H_C$-fragment of the TeNT, which were expressed in recombinant form and which revealed that the $H_{CC}$-, but not the $H_{CN}$ domain binds to neurons (see Herreros et al. (2000), Biochem. J. 347, 199-204). At a later stage, a single ganglioside binding site within the $H_{CC}$-domains of BoNT/A and B was localised and characterised (see Rummel et al. (2004), Mol. Microbiol. 51, 631-643). The site for binding the synaptotagmin I and II, identified as protein receptor for BoNT/B and G, could likewise be restricted to the region of the $H_{CC}$-domains of BoNT/B and G (see Rummel et al. (2004), J Biol Chem 279, 30865-70). Neither in PC12 cells nor in in vitro protein binding studies does BoNT/A show an interaction of any kind with the currently 13 members of the synaptotagmin protein family.

It is, therefore, the object of the present invention to provide means and processes for influencing the neurotoxicity of BoNT/A.

The object is attained by providing a polypeptide consisting of an amino acid sequence, at least 70% of which is identical to the amino acid sequence of the synaptic vesicle glycoprotein 2C of *homo sapiens* and by the fact that the polypeptide binds the $H_C$-fragment of botulinum neurotoxin A provided that the polypeptide is not the synaptic vesicle glycoprotein 2C of *homo sapiens*. The present invention further relates to the use of the polypeptide and its luminal domain as an antagonist for reducing the neurotoxicity of BoNT/A, as an expedient for identifying substances which reduce binding of BoNT/A to nerve cells and for detecting BoNT/A in various matrices.

The present invention now proposes the synaptic vesicle protein 2C (SV2C) as a receptor for BoNT/A.

The inventor was able to demonstrate in studies that neither synaptophysin, synaptoporin, synaptogyrin I & III, synaptic vesicle glycoprotein 2A (SV2A) nor synaptic vesicle glycoprotein 2B (SV2B) act as a protein receptor for BoNT/A. It was, however, possible to demonstrate binding of BoNT/A to SV2C.

In a ligand-receptor study the luminal domains of the proteins synaptophysin, synaptoporin, synaptogryin I & III, SV2A, SV2B and SV2C were sub-cloned and expressed in *E. coli* in recombinant form and isolated as glutathione-S-transferase-(GST)-fusion protein. The $H_C$-fragments of the seven BoNTs and of TeNT were both expressed in recombinant form in *E. coli* as well as translated in vitro with $^{35}$S-methionine. The affinity of the $H_C$-fragments to the luminal domains of the above listed GST-fusion proteins was determined in glutathione-S-transferase-(GST)-pull-down experiments. In the presence of GST-SV2C derivates the inhibition of neurotoxicity of BoNT/A and BoNT/B was analysed in the isolated nerve-muscle-preparation of the mouse (Hemi-Diaphragma-Assay=HDA) which represents the physiological target of clostridial neurotoxins.

The luminal domain of SV2C (amino acids 454-579), in particular, represents the fragment for an interaction with BoNT/A. The isolated 125mer peptide of the luminal domain can interact with the $H_C$-fragment of BoNT/A without a ganglioside. As a result of the interaction of the SV2C peptide with BoNT/A its receptor binding site is occupied and the interaction with SV2C, embedded in the membrane, is blocked. More specifically, the present invention includes a 125mer peptide, comprising the luminal domain of SV2C, or a peptide consisting of an amino acid sequence, at least 80% of which is identical to the luminal domain of SV2C or which is modified post-translationally. These agents may be employed for specific binding to the $H_C$-fragment of BoNT/A. As a result thereof, the receptor binding site of BoNT/A is occupied and its physiological interaction with SV2C, present in the plasma membrane, is inhibited. Thus, acute intoxication with BoNT/A may be prevented. In addition, these agents may be used in competitive binding studies in the search for other molecules likewise settling into the receptor binding site in the $H_C$-fragment of BoNT/A and acting, therefore, as antagonists. By marking the agents, e.g. with fluorophores or by specific identification sequences or by an immobilisation on solid matter phases, after binding of these agents to BoNT/A, the latter may be detected directly and specifically. Thus, it is possible to detect BoNT/A in a specific manner in various environments and matrices.

SV2C is a glycoprotein from nerve cells and neuroendocrine cells (synoptic article by: Janz, R. and Südhof T. C., Neuroscience 94 (1999), 1279-1290). It consists of 727 amino acids having a molecular weight of 86 kDa and is embedded with 12 trans-membrane domains in the membrane of synaptic vesicles. The amino terminus having a length of about 160 amino acids and the carboxyl terminus having a length of 11 amino acids are located in the cytosol as is a section between the trans-membrane domains 6 and 7 having a length of 90 amino acids. Intravesicularly, between the trans-membrane domains 7 and 8, there is only located a section having a length of 125 amino acids (amino acids 454-579), the intravesicular or luminal domain (LD) containing three putative N-glycosylation sites and two putative disulphide bridges. The role of SV2C as ion or sugar transporter in synaptic vesicles has not been confirmed, but an interaction—as a function of the phosphorylation of the amino terminus—of the three SV2 isoforms with those of the synaptotagmin is an indicator that via SV2 the quantity of free synaptotagmin for binding $Ca^{2+}$ and subsequent initiation of exocytosis is influenced.

The membrane of the synaptic vesicles merges with the pre-synaptic plasma membrane by exocytosis, causing the synaptic vesicle proteins to also be present in the pre-synaptic membrane for a short time. As a result thereof, the intravesicular domains of the synaptic vesicle proteins are exposed in an extracellular manner. Binding of the $H_C$-fragment of BoNT/A to the numerously occurring complex polysialogangliosides on the surface of the nerve cell is not sufficient on its own to accommodate the neurotoxin. However, by accumulating the BoNT/A molecules on the surface of the nerve cell, these can diffuse laterally in the membrane, increasing the probability of the productive encounter with the rarely exposed protein receptor. In the case of SV2C, the luminai domain having 125 amino acids is exposed extracellularly after vesicle fusion, thus being available to BoNT/A as a protein receptor. Since the neurotoxin, due to the ganglioside binding, resides quite closely above the membrane, the approximately 30 first and last amino acids of the luminal domain, analogously to the BoNT/B/G-synaptotagmin interaction, are preferably provided as receptor. After accommodating the receptor neurotoxin complex in the endosome, the latter is acidified, the translocation domain is inserted into the endosomal membrane, translocating the partially unfolded LC into cytosol, where the latter splits its specific substrate in the final step. The cycle of the complex formation and dissociation of the fusion proteins is interrupted, thereby inhibiting the release of acetylcholine. As a result thereof, striated muscles are paralysed and sweat glands cease their secretion. The active period of the individual BoNT serotypes varies, depending on the presence of intact LC in the cytosol.

That preferably the cholinergic transmission is blocked, may be explained by the fact that the peripheral HC penetrates the neuron. Central synapses are protected by the blood-brain-barrier which cannot be overcome by proteins.

In the following, terms are defined, which are to be understood in the context of the present application.

The botulinum neurotoxin A (BoNT/A) prepared in recombinant form from *E. coli*, which, inter alia contains the amino acid sequence identical to the native botulinum neurotoxin A, acts in a pharmacologically identical manner to the native BoNT/A and is referred to as recombinant botulinum neurotoxin wild type. The $H_C$-fragment of BoNT/A prepared in recombinant form has the same amino acid sequence as the corresponding native $H_C$-fragment and the same binding properties as the native BoNT/A. The nerve cells mentioned above are cholinergic motor neurons. Preferably, the transport protein binds specifically to the molecules associated with the plasma membrane, transmembrane proteins, synaptic vesicle proteins, a protein of the SV2 family, preferably SV2C, particularly preferably the luminal domain of SV2C. Binding is preferably determined in vitro. Particularly preferably the determination is performed by using GST-pull-down experiments which are elaborated on in detail in the examples.

The sequence of SV2C can be obtained by anybody from databases. The sequence ID for SV2C from *homo sapiens* reads inter alia GenBank NP055794, for SV2C from *Rattus norvegicus* inter alia GenBank NP113781, for SV2C from *Mus musculus* inter alia GenBank XP_127490.

In the present context, the term "polypeptide" signifies amino acid polymers consisting of at least two monomer units. The monomers may in this context be naturally occurring or not naturally occurring amino acids. Preferably, a polypeptide has at least 10 amino acid monomers. The individual amino acids may in this case be modified. The modifications may be of natural origin (e.g. post-translational) or may be introduced synthetically such as e.g. by glycosylation, di- and oligomerisation and by modifications of the Cys-residues.

"% identity", according to the invention, means % identity on the protein level, established by known procedures, e.g. computer-assisted sequence comparisons (BLAST) Basic Local Alignment Search Tool, S. F. Altschul et al., J. Mol. Biol. 215 (1990), 403-410. Preferred methods for determining the identity initially generate the greatest possible conformity with the studied sequences. If sequence pairs are compared to one another, it is also possible to use the programs GAP (Devereux, J. et al., Nucleic Acids Res. 12812)=: 387 (1987) and BestFit. The use of standard parameters is generally possible, particularly preferably these are:
Algorithm: Needleman and Wunsch, J. Mol. Biol. 4:443-453 (1970)
Comparative matrix: BLOSUM 62 from Henikoff and Henikoff, PNAS USA 89 (1992), 10915-10919
Gap Penalty: 12
Gap Length Penalty: 4

The term "antibody" includes classic antibodies, single-chain antibodies and antibody fragments. Preferred fragments in this context are F(ab)2 and F(ab).

The term "composition", besides mixtures, also includes fusion proteins. The polypeptide contained in the composition may be present in the form of a conjugate. In this context, conjugates with dyes, iron particles, epitopes such as Flag or HA-Tag, cross-linkers, affinity peptides or radioactive isotopes are preferred.

According to a preferred embodiment, at least 80% of the amino acid sequence of the polypeptide is identical to the amino acid sequence of the synaptic vesicle glycoprotein 2C of *homo sapiens*. The amino acid sequence, at least 90% of which is identical to the amino acid sequence of the synaptic vesicle glycoprotein 2C of *homo sapiens* is particularly preferred. The amino acid sequence, at least 95% of which is identical to the amino acid sequence of the synaptic vesicle glycoprotein 2C of *homo sapiens* is preferred in particular.

According to a further preferred embodiment, the amino acid sequence of the polypeptide differs from the amino acid sequence of the synaptic vesicle glycoprotein 2C of *h. sapiens* by the addition, substitution, deletion, insertion and/or inversion of at least one amino acid, preferably not more than 5 amino acids, in particular not more than 1 amino acid. The addition, substitution, deletion, insertion or inversion may in this context be performed in a manner known per se.

According to a further preferred embodiment, at least 70% of the amino acid sequence of the polypeptide is identical to the amino acid sequence of the luminal domain (amino acids 454-579) of the synaptic vesicle glycoprotein 2C of *homo sapiens*. One prefers the amino acid sequence, at least 80% of which is identical to the amino acid sequence of the luminal domain (amino acids 454-579) of the synaptic vesicle glycoprotein 2C of *homo sapiens*. One also prefers the amino acid sequence, at least 90% of which is identical to the amino acid sequence of the luminal domain (amino acids 454-579) of the synaptic vesicle glycoprotein 2C of *homo sapiens*. One prefers, in particular, the amino acid sequence, at least 95% of which is identical to the amino acid sequence of the luminal domain (amino acids 454-579) of the synaptic vesicle glycoprotein 2C of *homo sapiens*. In particular, the polypeptide is the isolated polypeptide of the luminal domain (amino acids 454-579) of the synaptic vesicle glycoprotein 2C of *homo sapiens*, the isolated polypeptide binding the $H_C$-fragment of botulinum neurotoxin A.

The present invention further provides nucleic acids coding the polypeptide according to the invention. Furthermore, vectors according to the invention are provided containing the nucleic acid according to the invention for the replication and optional expression under the control of an appropriate promoter in a suitable host cell. According to a further aspect of the present invention, a process for the preparation of the polypeptide according to the invention is provided, comprising the recombinant expression of a nucleic acid coding the polypeptide in a suitable host cell and, as the case may be, isolating the polypeptide prepared in a manner known per se.

The coding nucleic acid may in this context represent RNA, DNA or mixtures thereof. The nucleic acid, in view of its nuclease resistance, may furthermore be modified, e.g. by the insertion of phoshorthioate-bonds. The nucleic acid may be prepared from a parent nucleic acid, in which case this parent nucleic acid is accessible e.g. by cloning from genomic or cDNA-databases. Furthermore the nucleic acid may be prepared directly by solid phase synthesis. Suitable processes are known to the person skilled in the art. Provided one proceeds from a parent nucleic acid, a selective modification, e.g. by locality-specific mutagenesis, may be brought about, resulting in at least one addition, insertion, deletion and/or substitution on the amino acid level. The nucleic acid is then linked operatively to a suitable promoter. Suitable promoters for the expression in known expression systems are known to the person skilled in the art. The choice of promoter depends in this case on the expression system used for expression. In general, constitutive promoters are preferred, but inducible promoters may also be used. The construct prepared in this manner includes at least one part of a vector, in particular regulatory elements, the said vector being selected, for example, from γ-derivates, adenoviruses, baculoviruses, vaccinia viruses, SV40-viruses and retroviruses. The vector is preferably capable of expression of the nucleic acid in a given host cell.

The invention further provides host cells containing the vector and suitable for the expression of the vector. Numerous prokaryotic and eukaryotic expression systems are known in the state of the art, the host cells being selected, for example, from prokaryotic cells such as *E. coli* or *B. subtilis*, from eukaryotic cells such as *S. cerevisiae* and *P. pastoris* or even higher eukaryotic cells such as insect cells or mammal cells.

The peptide or polypeptide may also be obtained directly by synthesis or fragment condensation. Appropriate methods are known to the person skilled in the art.

The peptide or polypeptide is subsequently purified. Here, methods are used which are known to the person skilled in the art, such as e.g. chromatography methods or electrophoresis.

According to a further aspect of the present invention, a composition is provided including at least one polypeptide according to the invention. The composition may in this case also be present as a mixture or a conjugate. The polypeptide may, for example, be conjugated with dye molecules or excipients.

According to a further aspect of the present invention, an antibody or a fragment thereof is provided, which binds to the amino acid sequence, at least 70% of which is identical to the amino acid sequence of the luminal domain (amino acids 454-579) of the synaptic vesicle glycoprotein 2C of *homo sapiens*. The antibody may be monoclonal or polyclonal. Monoclonal antibodies may be prepared in accordance with processes known to the person skilled in the art, by immunising test animals such as mice, and by subsequently isolating and screening hybridoma.

Preferably, the antibody is capable of blocking the binding of the synaptic vesicle glycoprotein 2C to botulinum neurotoxin. This can be detected by known competitive assays such as radio-immuno-assays or ELISAs.

According to a further aspect of the present invention, a pharmaceutical composition is provided, including at least one polypeptide according to the invention and/or at least one antibody according to the invention. The pharmaceutical composition may optionally contain a pharmaceutically acceptable excipient, a diluent and/or an additive. The pharmaceutical composition is suited for oral, intravenous, subcutaneous, intramuscular and topical administration.

The pharmaceutical composition is indicated for treating botulism, after an overdose during therapeutic treatment or cosmetic application of BoNT/A, intoxication or for prophylactic purposes.

According to a further aspect of the present invention, a process for reducing the neurotoxicity of BoNT/A in mammals is provided, including administering an agent to a mammal, the agent reducing the binding of BoNT/A to an amino acid sequence, at least 70% of which is identical to the luminal domain (amino acids 454-579) of the synaptic vesicle glycoprotein 2C of *homo sapiens*, by at least 10%, preferably by at least 50%, in particular by at least 80%.

The agent can in this case be determined by the screening process described in what follows.

Preferably, a polypeptide is administered to a mammal, having an amino acid sequence, at least 70% of which is identical to the luminal domain (amino acids 454-579) of the synaptic vesicle glycoprotein 2C (SV2C) of *homo sapiens* and which reduces binding of BoNT/A to SV2C.

Furthermore, it is preferred to administer to the mammal an antibody, reducing binding of BoNT/A to an amino acid sequence, at least 70% of which is identical to the luminal domain (amino acids 454-579) of the synaptic vesicle glycoprotein 2C (SV2C) of *homo sapiens*.

Furthermore, it is preferred to administer to the mammal an agent, reducing the expression of the luminal domain (amino acids 454-579) of the synaptic vesicle glycoprotein 2C of *homo sapiens*. The agent may in this case be an antisense-molecule. Methods for the preparation of antisense-molecules are known to the person skilled in the art.

The process may be used for reducing the neurotoxicity of BoNT/A in botulism, after an overdose during therapeutic treatment or cosmetic application of BoNT/A, intoxication or for prophylactic purposes.

Preferably, the mammal is *homo sapiens*.

According to a further aspect of the present invention, a process for identifying an agent is provided, reducing binding of BoNT/A to the luminal domain (amino acids 454-579) of the synaptic vesicle glycoprotein 2C of *homo sapiens*, comprising:
(a) bringing into contact an agent with a solution of BoNT/A and GST-SV2C (454-579)
(b) determining the quantity of bound GST-SV2C (454-579)
(c) selecting an agent, which reduces the quantity of BoNT/A bound to GST-SV2C (454-579)

Screening may in this context e.g. be performed by means of chemical libraries. In addition, databases consisting of DNA and/or RNA molecules are likewise taken into consideration.

Preferably, the luminal domain (amino acids 454-579) of the synaptic vesicle glycoprotein 2 C of *homo sapiens* is embedded in a plasma membrane of a cell. In this context, appropriate cells are neuroendocrine cells such as PC12, neuroblastoma-cells such as 2A and hybridoma-cells from embryonal brain tissue such as NT2.

Furthermore, binding of BoNT/A to the synaptic vesicle glycoprotein 2C of *homo sapiens*, reduced by the presence of the agent, is preferably detected by decreased neurotoxicity of the BoNT/A in the Mouse Hemidiaphragma Test.

According to a further aspect of the present invention, the agent obtainable by the afore described process is provided.

According to a further aspect of the present invention a process is provided for detecting BoNT/A from *Clostridium botulinum* in any desired sample, comprising:
(a) immobilising a polypeptide on a solid phase, in which case the polypeptide has an amino acid sequence, at least 70% of which is identical to the luminal domain (amino acids 454-579) of the synaptic vesicle glycoprotein 2C of *homo sapiens* and which polypeptide reduces binding of BoNT/A to SV2C;
(b) bringing into contact of the immobilised polypeptide with a sample under conditions permitting binding of BoNT/A to the polypeptide;
(c) eluting the BoNT/A polypeptide complex; and
(d) detecting the complex or its elements.

Immobilisation may, for example, be performed by BrCn-coupling of the polypeptide to materials known for chromatography purposes, such as Sepharose. The conditions under which binding of BoNT/A to the polypeptide may take place, may be determined by routine tests. The conditions are to be selected so as not to denature any of the binding partners. Eluting may, for example, take place by competition or modification of the pH- and/or salt conditions. The complex and its elements may, for example, be separated by SDS-PAGE.

The following example serves merely for illustration purposes and is not to be considered limiting.

FIG. 1: The $H_C$-fragment of BoNT/A interacts with SV2C. (A) Schematic illustration of the synaptic vesicle glycoproteins. (B, C) GST-fusion proteins immobilised on GT-Sepharose micro-beads are incubated with recombinant (B) or $^{35}$S-marked (C) BoNT $H_C$-fragments in the presence of gangliosides. $H_C$-fragments bound to the solid phase are detected by SDS-PAGE and Coomassie blue staining or autoradiography.

Figure 2:
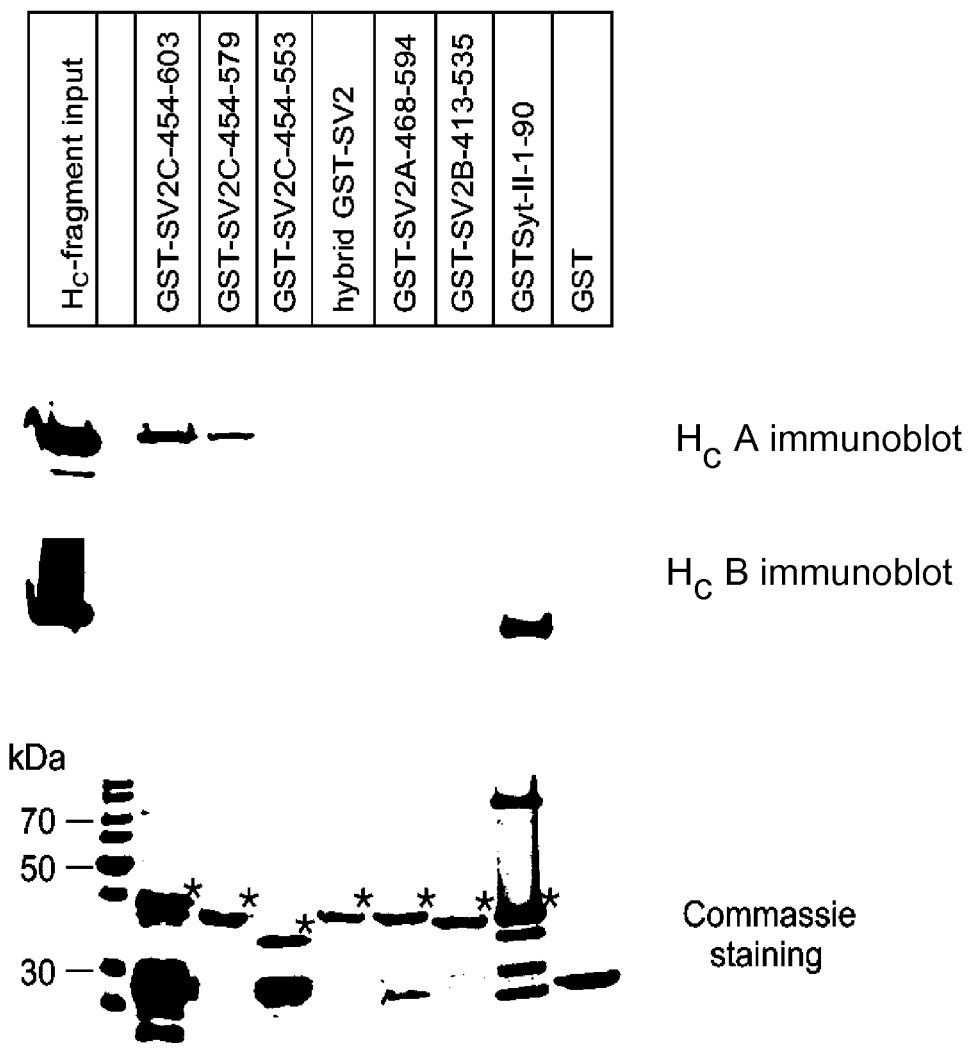

FIG. 2: BoNT/A $H_C$-fragment binds to the intravesicular region adjoining the transmembrane domain 8 of SV2C. GST-fusion proteins immobilised on GT-Sepharose micro-beads are incubated with recombinant BoNT $H_C$-fragments in the presence of gangliosides. $H_C$-fragments bound to the solid phase are detected by SDS-PAGE and Coomassie blue staining or by immuno-chemical methods.

MATERIAL AND METHODS

Plasmid Construction and Preparation of Recombinant Proteins

Plasmids for *E. coli* expression of the full-length form of BoNT/A and B or recombinant $H_C$-fragments of BoNT/A-G and TeNT respectively, with carboxyl-terminal StrepTag for affinity purification or, respectively, for in vitro transcription/translation with $^{35}$S-methionine were brought about by PCR-methods with appropriate primers, BoNT/A-G and TeNT coding cDNA and the expression vector pQe3 (Qiagen AG or pSP72 (Promega), respectively, serving as the starting vector.

cDNA sections coding the intravesicular segments of the various synaptic vesicle protein were cloned into the vector pGEX-4T3, using appropriate oligonucleotides and an embryonal mouse cDNA-database (GST-Syo-157-218, GST-Syg-I-45-98) or plasmids with appropriate cDNA as a basis: GST-Syg-I-127-169 (RZPD, Deutsches Ressourcenzentrum für Genomforschung GmbH; www.rzpd.de; ID IRAKp961C072Q), GST-SV2A-468-618 (RZPD-ID IRAKp961024100Q), GST-Syo-22-103 (Rat; T. C. Südhof, Dallas), GST-Syg-III-46-88 and GST-Syg-III-128-168 (Mouse; T. C. Südhof, Dallas), GST-SV2B-413-560 (Rat; S. Bajjalieh, Seattle), and GST-SV2C-454-603 (Rat; R. Janz, Houston). A plasmid coding the hybrid GST-SV2-C/A contains the amino acids 454-553 of SV2C and 568-594 of SV2A and was likewise generated by the corresponding oligonucleotides by PCR. The nucleic acid sequences of all plasmids were confirmed by DNA-sequencing. The recombinant $H_C$-fragments were prepared in the *E. coli* strain M15 [pRep4] (Qiagen) during induction for ten hours at room temperature and purified on a StrepTactin-matrix (IBA GmbH) in accordance with the manufacturer's instructions. The GST-fusion proteins obtained from *E. coli* BL21 were isolated with the aid of glutathione immobilised on Sepharose micro-beads. Fractions containing the desired proteins were combined and dialysed against Tris-NaCl-triton-buffer (20 mM Tris-HCl, 150 mM NaCl, 0.5% Triton X-100, pH 7.2), Kreb-Ringer buffer respectively (118 mM NaCl, 4.7 mM KCl, 1.2 mM $MgSO_4$, 1.2 mM $KH_2PO_4$, 25 mM $NaHCO_3$, 2.5 mM $CaCl_2$, 11 mM glucose).

$^{35}$S-labelled $H_C$-fragments were synthesised in vitro from pSP72 derivates, which were made linear downstream of the carboxyl-terminal codon of the neurotoxin, utilising the reticulocyte lysate system (Promega, Mannheim) and L-$^{35}$S-methionine (840 kBq, >37 TBq/mmol; Amersham Biosciences) in a batch of 2 µl.

GST-Pull-Down Assay

GST-fusion proteins (0.15 nmol each) which had been immobilised on 10 µl GT-Sepharose micro-beads, were incubated at 4° C. for 3 h with $H_C$-fragments (0.1 nmol) in the absence or in the presence of a bovine brain-ganglioside-mixture (18% GM1, 55% GD1a, 10% GT1b, 2% other gangliosides; Calbiochem; 20 µg each) in a total volume of 100 µl Tris-NaCl-triton-buffer. The micro-beads were collected by centrifuging, the supernatant was removed and the separated micro-beads were in each case rinsed three times with 160 µl of the same buffer. The rinsed pellet fractions were boiled in SDS-sample buffer and studied, together with the supernatant fractions, by SDS-PAGE and Coomassie blue staining, autoradiography or immuno-blotting.

Mouse Hemidiaphragma Assay (HDA)

The Mouse Hemidiaphragma Assay (HDA) was performed as described in Habermann (Habermann E, Dreyer F, Bigalke H (1980) Tetanus toxin blocks the neuromuscular transmission in vitro like botulinum A toxin. Naunyn Schmiedebergs Arch Pharmacol 311:33-40). The nervus phrenicus was stimulated by one Hertz and the contraction amplitude recorded continuously by means of a potency meter and the VitroDat Online Software (FMI GmbH, Seeheim-Ober Beerbach). After adding the BoNTs, the time was measured during which the contraction amplitude drops to 50% of the output value (paralytic half-time). Full-length scBoNT/A wild type was measured at least threefold in the following final concentrations: 24.3 pM, 72.8 pM, 223 pM and 728 pM. A potency function was approximated to this concentration-effect-relationship.

$y(A)=225.87x^{-0.2573}$ ($R^2=0.9627$). In the same manner the concentration-effect-relationship $y(B)=423.59x^{-0.297}$ ($R^2=0.983$) was established for full-length scBoNT/B wild type having the following final concentrations: 100 pM, 300 pM, 1000 pM and 3000 pM. For the inhibition studies scBoNT/A (223 pM) and scBoNT/B (1000 pM), either with GST-SV2C-454-579 or GST-SV2-C/A (final concentration 4, 7 or 11 µM) were mixed, incubated at 20° C. for 15 minutes and added to the HDA. Based on the potency functions the partially extended paralytic half-times were converted to correspondingly lower neurotoxin doses and expressed as % toxicity.

Results

The luminal domains and the carboxyl-terminal transmembrane domains of the proteins synaptophysin, synaptoporin, synaptogyrin I & III, synaptotagmin II, SV2A, SV2 and SV2C were sub-cloned and expressed in *E. coli* in recombinant form and isolated as glutathione-S-transferase (GST)-fusion protein. The $H_C$-fragments of the seven BoNTs and of Tetanus neurotoxin (TeNT) were both expressed in *E. coli* in recombinant form as well as translated in vitro with $^{35}$S-methionine. The affinity of the $H_C$-fragments to the luminal domains of the above mentioned GST-fusion proteins was determined in glutathione-S-transferase (GST)-pull-down experiments. For this purpose, the respective GST-fusion protein having different $H_C$-fragments was incubated and a phase separation was performed. Free $H_C$-fragment remained in the separated supernatant, while bound BoNT $H_C$-fragment could be detected in the solid phase, together with the GST-fusion protein. Substitution of the recombinant $H_C$-fragments by $^{35}$S-labelled $H_C$-fragments as well as by full-length BoNT/A showed the same results in the GST-pull-down assay when compared with the $H_C$-fragment BoNT/A.

TABLE 1

The intravesicular domain of SV2C blocks the activity of BoNT/A in the HDA.

| BoNT | BoNT [pM] | Inhibitor[a] | Inhibitor [µM] | Paral. half-time value $t_{1/2}$[b] [min] | Toxicity versus pure BoNT [%] | Inhibition [%] |
|---|---|---|---|---|---|---|
| BoNT/A | 223 | none | | 50 ± 7 | 100 | |
| BoNT/A | 223 | SV2C-454-579 | 4.7 | 72 ± 3 | 25.1 ± 1.0 | 75 |
| BoNT/A | 223 | SV2C-454-579 | 11.2 | 83 ± 8 | 14.6 ± 1.5 | 85 |

TABLE 1-continued

The intravesicular domain of SV2C blocks the activity of BoNT/A in the HDA.

| BoNT | BoNT [pM] | Inhibitor[a] | Inhibitor [μM] | Paral. half-time value $t_{1/2}$[b] [min] | Toxicity versus pure BoNT [%] | Inhibition [%] |
|---|---|---|---|---|---|---|
| BoNT/A | 1000 | none | | 57 ± 6 | 100 | |
| BoNT/A | 1000 | SV2C-454-579 | 4.7 | 56 ± 13 | 105.1 ± 24.8 | 0 |
| BoNT/A | 1000 | SV2C-454-579 | 11.2 | 60 ± 7 | 86.6 ± 9.7 | 14 |
| BoNT/A | 223 | SV2-C/A | 4.7 | 51 ± 4 | 100.0 ± 1.0 | 0 |
| BoNT/A | 223 | SV2-C/A | 11.2 | 51 ± 5 | 100.0 ± 1.0 | 0 |

[a]Inhibitors were used as GST-fusion proteins
[b]mean values ± S.D. (n = 3-9)
[c]Full-length scBoNT/A wild type was measured at least three-fold in the following final concentrations: 24.3 pM, 72.8 pM, 223 pM and 728 pM. To this concentration-effect-relationship a potency function was approximated: $y(A) = 225.87x^{-0.257/3}$ ($R^2 = 0.9627$). In the same manner the concentration-effect-relationship $y(B) = 423.59x^{-0.297}$ ($R^2 = 0.983$) was established for full-length scBoNT/B wild type having the following final concentrations: 100 pM, 300 pM, 1000 pM and 3000 pM.

In this context, it was found that none of the eight $H_C$-fragments of BoNT/A, B, C1, D, E, F, G and TeNT binds to the luminal domains of synaptophysin, synaptoporin, synaptogyrin I & II, SV2A and SV2B, regardless of the presence of complex gangliosides. As already known, the $H_C$-fragments of BoNT/B and G bind to the luminal domain of synaptotagmin II, but not the $H_C$-fragment of BoNT/A. Only the recombinant as well as the $^{35}$S-labelled $H_C$-fragment as well as the full-length BoNT/A bind specifically to the luminal domain of SV2C fused to GST, regardless of the presence of complex gangliosides. All other $H_C$-fragments show no interaction with SV2C (FIG. 1).

It has furthermore been shown that binding of the $H_C$-fragment of BoNT/A to the luminal domain of SV2C is weaker after shortening by the transmembrane domain 8 (GST-SV2C 454-579) (FIG. 2). A carboxyl-terminal deletion by 20 amino acids (GST-SV2C 454-553) and further shortenings resulted in the interaction with BoNT/A coming to a stop. Amino-terminal deletions prevented binding of BoNT/A to the GST-SV2C fusion proteins as well.

The GST-fusion proteins of SV2A and SV2B, homologous to SV2C, showed no binding to BoNT/A, neither with nor without carboxyl-terminal transmembrane domain. The generation of a hybrid consisting of GST, the amino acids 454-554 of SV2C and the amino acids 568-594 of SV2A likewise no longer exhibited any interaction with the BoNT/A $H_C$-fragment.

The invention claimed is:

1. An isolated polypeptide, wherein the amino acid sequence of the polypeptide comprises the amino acid sequence of SEQ ID NO: 1, and further wherein the isolated polypeptide binds the $H_C$-fragment of botulinum neurotoxin A (BoNT/A), with the proviso that a polypeptide comprising the amino acid sequence of full-length synaptic vesicle glycoprotein 2C (SV2C) of *Homo sapiens* is excluded.

2. A composition comprising a polypeptide according to claim 1.

3. A process for reducing the neurotoxicity of BoNT/A in a mammal, comprising administering the isolated polypeptide of claim 1 to the mammal.

4. The process according to claim 3, wherein the process is used for reducing the neurotoxicity of BoNT/A in botulism or after an overdose during therapeutic treatment or cosmetic application of BoNT/A.

5. The process according to claim 3, wherein the mammal is *Homo sapiens*.

6. A process for identifying an agent that reduces binding of BoNT/A to the luminal domain (amino acids 454-579) of the synaptic vesicle glycoprotein 2C of *Homo sapiens*, comprising:
   (a) bringing into contact an agent with a solution of BoNT/A and the isolated polypeptide of claim 1,
   (b) determining the quantity of bound isolated polypeptide; and
   (c) selecting an agent, which reduces the quantity of BoNT/A bound to the isolated polypeptide.

7. The process according to claim 6, wherein the isolated polypeptide is embedded in a plasma membrane of a cell.

8. The process according to claim 6, wherein binding of BoNT/A to the isolated polypeptide is detected by decreased neurotoxicity of the BoNT/A in a Mouse Hemidiaphragma Test.

9. A process for detecting BoNT/A from *Clostridium botulinum* in any desired sample, comprising:
   (a) immobilising the isolated polypeptide of claim 1 on a solid phase;
   (b) bringing into contact of the immobilised polypeptide with a sample under conditions permitting binding of BoNT/A to the immobilized polypeptide;
   (c) eluting the BoNT/A polypeptide complex; and
   (d) detecting the complex or its elements.

10. A fusion protein comprising:
    (a) the luminal domain of the synaptic vesicle glycoprotein 2C (SV2C) of *Homo sapiens*, wherein the luminal domain of SV2C has the amino acid sequence of SEQ ID NO: 1, and further wherein the luminal domain of SV2C binds the Hc-fragment of botulinum neurotoxin A; and
    (b) a heterologous amino acid sequence, wherein the heterologous sequence is an epitope or an affinity peptide, with the proviso that the fusion protein does not comprise the full-length amino acid sequence of synaptic vesicle glycoprotein 2C (SV2C) of *Homo sapiens*.

11. The fusion protein of claim 10, wherein the epitope or the affinity peptide is selected from a group consisting of a Flag-tag, a HA-tag, and a GST tag.

12. The fusion protein of claim 10, wherein the heterologous sequence is a Flag-tag.

13. The fusion protein of claim 10, wherein the heterologous sequence is a HA-tag.

14. The fusion protein of claim 10, wherein the heterologous sequence is a GST-tag.

15. A composition comprising the fusion protein of claim 10.

16. A process for detecting BoNT/A in a sample, comprising:
    (a) immobilizing the fusion protein of claim 10 onto a solid phase;
    (b) bringing into contact the immobilized fusion protein with a sample containing BoNT/A under conditions permitting binding of BoNT/A to the fusion protein, wherein a complex of BoNT/A and the fusion protein is formed;
    (c) eluting the complex of BoNT/A and the fusion protein;
    (d) quantifying the BoNT/A present in the complex.

17. The process of claim 16, wherein the epitope or the affinity peptide is selected from a group consisting of a Flag-tag, a HA-tag, and a GST-tag.

18. The process of claim 16, wherein the heterologous sequence is a Flag-tag.

19. The process of claim 16, wherein the heterologous sequence is a HA-tag.

20. The process of claim 16, wherein the heterologous sequence is a GST-tag.

21. The isolated polypeptide of claim 1, wherein the isolated polypeptide is a 126mer consisting of the amino acid sequence of SEQ ID NO: 1.

22. A composition comprising the fusion protein of claim 12.

23. A composition comprising the fusion protein of claim 13.

24. A composition comprising the fusion protein of claim 14.

* * * * *

SEQUENCE LISTING

```
<160> NUMBER OF SEQ ID NOS: 1

<210> SEQ ID NO 1
<211> LENGTH: 126
<212> TYPE: PRT
<213> ORGANISM: Homo sapiens
<220> FEATURE:
<221> NAME/KEY: DOMAIN
<222> LOCATION: (1)...(126)
<223> OTHER INFORMATION: luminale domain 454-579 of SV2C

<400> SEQUENCE: 1

Phe Pro Asp Val Ile Lys Pro Leu Gln Ser Asp Glu Tyr Ala Leu Leu
 1               5                  10                  15

Thr Arg Asn Val Glu Arg Asp Lys Tyr Ala Asn Phe Thr Ile Asn Phe
                20                  25                  30

Thr Met Glu Asn Gln Ile His Thr Gly Met Glu Tyr Asp Asn Gly Arg
            35                  40                  45

Phe Ile Gly Val Lys Phe Lys Ser Val Thr Phe Lys Asp Ser Val Phe
        50                  55                  60

Lys Ser Cys Thr Phe Glu Asp Val Thr Ser Val Asn Thr Tyr Phe Lys
65                  70                  75                  80

Asn Cys Thr Phe Ile Asp Thr Val Phe Asp Asn Thr Asp Phe Glu Pro
                85                  90                  95

Tyr Lys Phe Ile Asp Ser Glu Phe Lys Asn Cys Ser Phe Phe His Asn
                100                 105                 110

Lys Thr Gly Cys Gln Ile Thr Phe Asp Asp Asp Tyr Ser Ala
            115                 120                 125
```